United States Patent [19]

Feinland et al.

[11] 4,119,399

[45] Oct. 10, 1978

[54] COMPOSITION FOR COLORING HAIR CONTAINING AN OXIDIZING AGENT AND CERTAIN QUATERNARY AMINES

[75] Inventors: Raymond Feinland, Stamford, Conn.; Stanley Pohl, New Rochelle; Michael Hnatchenko, Bronx, both of N.Y.

[73] Assignee: Clairol Incorporated, New York, N.Y.

[21] Appl. No.: 796,115

[22] Filed: May 11, 1977

Related U.S. Application Data

[62] Division of Ser. No. 656,503, Feb. 9, 1976.

[51] Int. Cl.$^2$ ............................................. A61K 7/13
[52] U.S. Cl. ........................................ 8/10.2; 8/10.1; 8/11; 8/32; 8/85 R; 424/70
[58] Field of Search ................... 8/10.2, 32, 11, 85; 424/70

[56] References Cited

U.S. PATENT DOCUMENTS

| 3,104,933 | 9/1963 | Mendelsohn | 8/85 |
| 3,369,970 | 2/1968 | McLaughlin et al. | 8/10.1 |
| 3,577,528 | 5/1971 | McDonough et al. | 424/70 |
| 3,642,423 | 2/1972 | Bil et al. | 8/10.2 |
| 3,822,312 | 7/1974 | Sato et al. | 424/70 X |
| 3,884,627 | 5/1975 | Brody et al. | 8/10.2 |
| 3,891,385 | 6/1975 | Kalopissis et al. | 8/10.1 |
| 3,930,792 | 1/1976 | Alperin et al. | 8/10.1 |

FOREIGN PATENT DOCUMENTS 758,762 10/1956 United Kingdom ................... 424/62

Primary Examiner—Albert T. Meyers
Assistant Examiner—Vera C. Clarke
Attorney, Agent, or Firm—Irving Holtzman; George A. Mentis; David J. Mugford

[57] ABSTRACT

A composition for coloring hair comprising a liquid vehicle, an oxidizing agent and at least one di-long chain aliphatic hydrocarbon quaternary amine compound and a method for coloring hair using this composition.

27 Claims, No Drawings

COMPOSITION FOR COLORING HAIR CONTAINING AN OXIDIZING AGENT AND CERTAIN QUATERNARY AMINES

This is a division of application Ser. No. 656,503, filed 2/9/76.

This invention relates to an oxidizing agent containing compositions designed to simultaneously condition and change the color of the keratinic fibers and especially human hair on the head. More particularly, it concerns an aqueous composition containing an oxidizing agent, at least one quaternary amine compound defined in more detail below and optionally, one or more oxidation dye intermediates. When the oxidation dye intermediate is absent, the action of the composition on the hair will be lightening of it in conjunction with its conditioning. If one or more oxidation dye intermediates are present in the composition, the oxidizing agent will also serve to develop the color of the dye intermediates and to dye the hair.

Often after lightening or dyeing hair with aqueous compositions containing an oxidizing agent, the hair is left in an unsatisfactory condition with regard to its feel and combability. The hair often loses its smooth and soft texture. Moreover, relatively large forces have to be exerted on a comb in order to pass it through hair which has been subjected to these treatments.

It has now been found that these disadvantages can be avoided if there is also incorporated in the oxidizing agent containing composition used to treat the hair, a quaternary amine compound of the general formula:

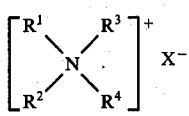  (I)

in which $R^1$ and $R^2$ are long chain aliphatic hydrocarbon radicals (e.g. alkyl radicals) having about 10 to 26 carbons (and preferably about 12 to 18 carbons), $R^3$ and $R^4$ are lower alkyl radicals having about 1 to 5 carbons and X is an anion. Human hair treated with such a composition has a smoother and softer feel and is easier to comb both when wet and dry, when compared with hair treated with similar compositions that do not contain said quaternary amine compound.

It has also been found that it is sometimes advantageous to incorporate in said composition, in addition to the quaternary amine of Formula I, a mono-long chain aliphatic hydrocarbon quaternary amine of formula:

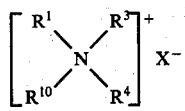  (Ia)

wherein $R^1$, $R^3$ and $R^4$ and $X^-$ have the values ascribed to them above and $R^{10}$ also have the value of $R^3$ and $R^4$.

It has been suggested in the prior art to incorporate certain quaternary amine compounds in hair dye compositions. However, there is nothing in the prior art that teaches the advantage of using a quaternary amine compound of Formula I in conjunction with an oxidizing agent as provided for herein.

South African Patent 73/5345 and U.S. Pat. No. 3,930,792 teach direct dyeing hair dye compositions, as distinguished from oxidation dye compositions, that employ certain quaternary amine compounds. However, in this case the quaternary amine is a mono-long chain alkyl quaternary compound.

U.S. Pat. Nos. 3,369,970, 3,884,627 and 3,642,423 show the use of certain quaternary amine compounds as surface active agents in certain dyeing compositions. However, again the use of the quaternary amine of Formula I above is not shown.

U.S. Pat. Nos. 3,155,591 and 3,272,712 show the use of certain quaternary amines as hair conditioning agents in hair rinse compositions. These, however, are not oxidizing agents containing compositions as is characteristic of the present invention.

In addition to the above, the following U.S. Patents are of interest, but do not appear any more pertinent than the art discussed above: Nos. 2,283,350; 2,759,975; 3,104,933; 3,822,312; 3,882,114 and 3,891,385.

The compositions of the present invention are usually prepared in two parts. One part, referred to herein as the base, will ordinarily contain the dyeing or lightening aids. In the embodiments of this invention in which the compositions also contain one or more oxidation dye intermediates, these will also be contained in the base. The second part of the composition, referred to herein as the oxidizer, will ordinarily contain the oxidizing agent and the carrier, therefore, which will usually be an aqueous carrier. It may also contain other ingredients such as a stabilizer for the oxidizing agent, etc. The compositions of the present invention are employed by mixing the aforesaid two parts together just before use. The mixture, so formed, is then applied to the head as described in more detail below.

As noted above, an essential feature of the compositions of this invention is the incorporation therein of one or more quaternary amine compounds defined generally in Formula I above. A variety of compounds falling within this formula may be used for the present purposes. By way of illustrating the various values that $R^1$, $R^2$, $R^3$, $R^4$ and X may have in the quaternary amines employable herein, the following are given:

(1) $R^1$ or $R^2$ may be n-decyl; lauryl, myristyl, palmityl, stearyl, behenyl, cerotyl, $\Delta^9$-decylenyl, $\Delta^9$-dodecylenyl, palmitoleyl, oleyl, linoleyl, linolenyl, erucyl, etc.

(2) $R^3$, $R^4$ or $R^{10}$ may be ethyl, methyl, n-propyl, i-propyl, n-butyl, sec. butyl, tert. butyl, n-pentyl.

(3) X may be an inorganic or organic ion including hydroxide (i.e. OH—), halide (e.g. chloride, bromide, iodide, fluoride); sulfate, phosphate; sulfonate; alkanoate (e.g. acetate, n-propionate, lactate, gluconate); lower alkyl sulfate (i.e. —$SO_4R_5$ wherein $R_5$ is lower alkyl having 1 to 5 carbons e.g. —$SO_4CH_3$; —$SO_4C_2H_5$; —$SO_4(CH_2)_2CH_3$; —$SO_4CH(CH_3)_2$, etc.

To more particularly illustrate the quaternary amine compounds that are useful for the purposes of the present invention, mention may be made of the following: distearyl dimethyl ammonium chloride, dilauryl dimethyl ammonium chloride, di-hydrogenated beef-tallow dimethyl ammonium chloride, dicetyl diethyl ammonium ethyl sulfate, dilauryl dimethyl ammonium chloride, ditallow dimethyl ammonium metyl sulfate, disoya dimethyl ammonium chloride, dicoco dimethyl ammonium chloride, etc. and mixtures thereof.

The quantity of said quaternary amine compound that will be contained in the compositions of this invention may vary somewhat. Ordinarily, it will constitute about 0.05% to 5.0% by weight based on the total final weight of the composition i.e. the total weight of the composition formed by mixing the base and the oxidizer.

The second essential component of the present composition is the oxidizing agent. The kind of oxidizing agent employed will be dependent upon the specific use to which the composition is going to be put. By way of illustrating particular oxidizing agents that are of interest herein, mention may be made of hydrogen peroxide, urea peroxide, melamine peroxide, sodium perborate, sodium percarbonate and sodium persulfate. However, the preferred oxidizing agent is hydrogen peroxide.

The quantity of oxidizing agent contained in the present compositions will vary with the particular agent selected and the specific use that the composition will be put to. Ordinarily, this will amount to about 0.5% to 20% by weight based on the total weight of the composition. When hydrogen peroxide is employed, the preferred range is about 2% to 4% by weight based on the total weight of the composite product.

It is a feature of one aspect of this invention to include in the present compositions one or more oxidation dye intermediates suitable for dyeing human hair. In this instance, the oxidizing agent contained therein will also serve, among other things, to develop the color in the dye intermediates and to facilitate the dyeing of the hair.

Oxidation dye intermediates that are useful in dyeing human hair and that may be employed in the present invention are well known in the prior art. Typical dye intermediates of this kind and combinations thereof made to obtain certain desired shades are disclosed in Tables IV, V and VI pages 308–310 of "Cosmetics Science and Technology" 2nd Edition, Volume 2, edited by Edward Sagarin, Interscience Publishers, Inc. New York, 1972. These are also useful for the present purposes and accordingly, said Tables IV, V and VI of Sagarin are specifically incorporated in this specification by way of reference.

Other oxidation dye intermediates that may be used herein are disclosed in U.S. Pat. No. 3,884,627. Of special interest are the so-called para components which are described in said patent as being of formula:

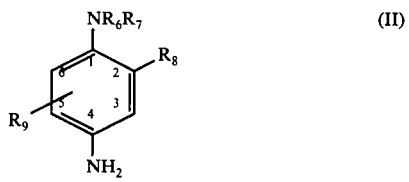

or their acid addition salts in which:
$R_6$ is alkyl or hydroxyalkyl;
$R_7$ is hydrogen or hydroxyalkyl;
$R_8$ is hydrogen, alkyl, alkoxy or halogen; and
$R_9$ occupies any one of the remaining positions on the benzene radical and is hydrogen, alkyl, alkoxy or halogen; providing that $R_7$ is hydrogen when $R_8$ is alkyl, alkoxy or halogen and providing that at least two of $R_6$, $R_7$, $R_8$ or $R_9$ are other than hydrogen.

Any compound falling within the definition of Formula II above is suitable for the present purposes. When $R_6$, $R_7$, $R_8$ or $R_9$ is alkyl in said formula, it may be any of a variety of alkyl groups. Thus, it may be a straight chain or branched chain alkyl radical which is preferably lower alkyl e.g. having from 1 to 6 carbon atoms. By way of illustration, the following alkyl groups may be mentioned as typical examples: methyl, ethyl, n-propyl, isopropyl, n-butyl, sec. butyl, tert. butyl, n-amyl, isoamyl, n-hexyl and the like.

In the case where $R_6$ or $R_7$ is a hydroxyalkyl radical in Formula II, it may be a monohydroxy, dihydroxy, trihydroxy, or other polyhydroxyalkyl radical. The alkyl chain is preferably a lower alkyl chain having from 2 to 6 carbon atoms. Typical mono and polyhydroxyalkyl radicals of this character are: 2-hydroxyethyl; 3-hydroxypropyl; 2-hydroxypropyl; tris (hydroxymethyl)methyl; 1,3-dihydroxy-2-methyl-propyl; 2,3-dihydroxypropyl; 1,3-dihydroxy-2-propyl, etc.

When $R_8$ or $R_9$ is halogen in Formula II, it can be any halogen atom e.g. Cl, Br, I, or F. When it is alkoxy, the alkoxy group will usually contain 1 to 6 carbon atoms, e.g. methoxy, ethoxy, n-propoxy, isopropoxy, n-butoxy, n-amyloxy, isoamyloxy, isobutoxy, etc.

To illustrate still more specific examples of para components falling within Formula II above that are particularly suitable for use in this invention, the following may be mentioned: N-ethyl-N-hydroxyethyl-p-phenylenediamine and its hydrochloride; N,N-bis(β-hydroxyethyl)-p-phenylenediamine and its hydrochloride or sulfate; N,N-bis(β-hydroxyethyl)-3-methyl-p-phenylenediamine and its hydrochloride or sulfate, N,3-dimethyl-p-phenylenediamine and its hydrochloride; N-hydroxyethyl-2-methyl-p-phenylenediamine and its hydrochloride; N,2-dimethyl-p-phenylenediamine; $N^1$-methyl-3-methoxy-p-phenylenediamine; $N^1$-methyl-2-methoxy-p-phenylenediamine; 3-chloro-$N^1$-methyl-p-phenylenediamine, N,N-bis(2,3-dihydroxypropyl)-p-phenylenediamine.

It is within the purview of the present invention to employ the para components of Formula II or the more conventional para component oxidation dye intermediates e.g. p-toluenediamine, p-aminophenol, p-aminodiphenylamine, 4-4'-diaminodiphenylamine, p-phenylenediamine, 2,6-dimethyl-p-phenylenediamine and 2,5-diaminopyridine. It is also contemplated by this invention that both types of para components may be employed together. It is further contemplated that these may also be used together with other oxidation dye intermediates which chemically couple with said para components under oxidative conditions. These coupling components comprise a well-known class of compounds in the hair dye art which are known to react oxidatively (i.e. with the aid of an oxidizing agent) with paradiaminobenzene compounds to produce dyes.

A number of very different types of chemical compounds are known to function as coupling components. The most important are phenols, m-phenylenediamines, m-aminophenols and compounds containing active methylene groups.

Phenols react with para components, in the presence of oxidizing agents, to produce indophenols. These are usually blue or violet compounds, although resorcinols give yellow or brown colored compounds under these conditions. The brown colors obtained from the reaction of resorcinols are commonly used to produce the depth of a shade. Examples of phenols useful in oxidation dye compositions of this invention are pyrogallol, resorcinol, pyrocatechol and alpha-naphthol.

m-Phenylenediamines give indamines on oxidative coupling with the para components and these are generally blue or violet compounds that can be used to modify a shade; usually they are employed to make a shade less warm. Examples of m-phenylenediamines commonly useful in the present oxidation dye compositions are m-phenylenediamine and 2,4-diaminoanisole.

m-Aminophenols can give either indophenols or indiamines on oxidative coupling with para components of this invention; however, it seems likely that indophenols are the preferred product. The products are usually violet in color and are used in modifying shades. Examples of aminophenols useful herein are 2,4-diaminophenol, m-aminophenol, aminoresorcinol, 1,5-aminohydroxynaphthalene and 1,8-aminohydroxynaphthalene.

Compounds containing active methylene groups are also capable of reacting with the oxidatively activated para components. The products are imino compounds of various types and are yellow or red in color. Examples of active methylene compounds employable in the present invention are 3-methylpyrazolone-(5), 1-phenyl-3-methylpyrazolone-(5), 1,3-dimethylpyrazolone-(5), acetoacetic acid anilide, benzoylacetotoluide and nicotinoylaceanilide.

Still other oxidation dye intermediates may be present in the compositions of this invention which produce colored products under oxidative conditions by more complex mechanisms. This may include one or more of self-coupling, or coupling with the para components or with other intermediates present. Among these may be mentioned hydroquinone, catechol, 1,5-naphthalenediol, and o-aminophenol.

It is sometimes desirable to add to the base of this invention dyes which are already colored i.e. which do not require an oxidizing agent for color development. These are generally added for blending purposes to obtain natural-looking colors in the final dyeing operation. One class of dyes which may be used for this purpose is the nitro dyes and this component is generally referred to herein as the "nitro dye component". A large number of nitro dyes are known in the prior art which are suitable for this purpose. A limitation that is placed on a nitro dye to be useful in the present invention is that it be one whose color is not destroyed by the oxidizing agent used in the final color development of the oxidizable components. By way of illustrating suitable nitro dyes, mention may be made of the following: 4-nitro-o-phenylenediamine, 2-nitro-p-phenylenediamine, 4-nitro-2-aminophenol, 5-nitro-2-aminophenol, 2-nitro-4-aminophenol and picramic acid.

The compositions of this invention may also advantageously have incorporated therein typical hair lightening and dyeing aids that are well known in this art. These will, for the most part, be in the base that is to be mixed with the oxidizer just before use as described above. Thus, for example, the conventional alkaline agents, thickening agents, solvents, buffers, antioxidants, sequestering agents, perfumes, etc. may be beneficially used.

However, since quaternary amines may be deactivated by certain large anionic groups, additives containing these groups are to be avoided. With this in mind, in selecting a surfactant it is well to employ a non-ionic or neutral surfactant. These will include such classes of surfactants as the long chain fatty acid alkanolamides or dialkanolamides, ethoxylated alkyl phenols, ethoxylated fatty alcohols and amphoteric surfactants (e.g. Miranols, betaine). More specifically, the following non-ionic surfactants may be mentioned by way of illustration: lauric diethanolamide, linoleic diethanolamide, glyceryl stearate, polyoxyethylene lanolin ether, polyoxyethylene oleyl ether, polyoxyethylene lauryl ether, polyoxyethylene nonyl phenol ether, polyoxyethylene stearate, polyoxyethylene tallate.

The pH of the compositions of this invention will generally be on the basic side e.g. 8–11. It is preferred, however, that this pH be in the range of about 9–10.

Any of a wide variety of alkalizing agents can be used to adjust the pH of the dyeing composition on the basic side. Ammonium hydroxide, because of its freedom from toxicity over a wide concentration range and its economy, is an acceptable alkalizing agent. However, there can be used in place of, or together with, ammonia any other compatible ammonia derivative as an alkalizing agent, such as an alkylamine, such as ethylamine, or triethylamine; or alkanolamine, such as monoethanolamine, diethanolamine, aminomethyl propanol, aminomethyl propanediol and trishydroxymethyl aminomethane. Likewise, any other of the common alkalizing agents may be used, such as sodium or potassium hydroxide, sodium or potassium carbonate, sodium phosphate, sodium hydrogen phosphate, sodium silicate and the like.

Various organic solvents may also be present in the instant composition for the purpose of solubilizing an oxidation dye intermediate or any other component which may be insufficiently soluble in water. Generally, the solvent selected is such as to be miscible with water and innocuous to the skin, and includes for example, ethanol, isopropanol, glycerine, ethylene glycol, propylene glycol, ethylene glycol monoethyl ether, diethylene glycol, diethylene glycol monoethyl ether, etc.

To exemplify the thickening agents that can also be incorporated in the present composition, mention may be made of sodium alginate or gum arabic, or cellulose derivatives, such as methyl cellulose or hydroxyethyl cellulose, or inorganic thickeners such as bentonite.

To illustrate the antioxidants that may be used in the present invention, mention may be made of sodium sulfite, thioglycollic acid, sodium hydrosulfite and ascorbic acid. Water is ordinarily a major constituent of the present composition and can vary over a wide range dependent in large measure on the quantity of other additives.

The compositions of this invention are preferably aqueous compositions. The term "aqueous composition" is used herein in its usual generic sense as embracing any water-containing composition embodied in the invention. This includes true solutions or mixtures of the dye in an aqueous medium, either alone or in conjunction with other materials, which are also dissolved or dispersed in the aqueous medium. The dye may be colloidally dispersed in the medium or may merely be intimately mixed therein.

To summarize the various components that may comprise the compositions of this invention, Table I below is given. The percentages are given as percent by weight based on the total weight of the composite composition.

TABLE I

| Components | % by weight | |
|---|---|---|
| | General | Preferred |
| Quaternary amine of Formula I | About .05 to 5 | About 0.1 to 3 |
| Oxidizing agent | About 0.5 to 20 | About 2 to 4 |
| Para components | About 0 to 3 | About 0 to 2 |
| Coupling component | About 0 to 3 | About 0 to 2 |
| Other oxidation dye intermediate | About 0 to 0.5 | About 0 to 0.3 |
| Nitro dyes | About 0 to 1 | About 0 to 0.5 |
| Neutral surfactant | About 0 to 30 | About 0 to 20 |
| Thickening agent | About 0 to 4 | About 0 to 2 |
| Antioxidants | About 0 to 1 | About 0 to 0.5 |
| Organic solvents | About 0 to 40 | About 0 to 20 |
| Water | QS to 100% | |

TABLE I-continued

| Components | % by weight | |
|---|---|---|
| | General | Preferred |
| Alkalizing agent to pH | About 8 to 11 | About 9 to 10 |

As mentioned above, the bases used in this invention are intended to be mixed with the oxidizing components which contain the oxidizing agent necessary to lighten the hair or to effect reaction to produce colored products. Typical oxidizers that are useful for this purpose are aqueous solutions of the oxidizing agent e.g. (hydrogen peroxide 5 to 12%).

In use, the mixture of base component and oxidizer component is well shaken and applied to the hair. It can be applied as a shampoo to the entire head or applied to one area of the hair, such as the roots and combed through the rest of the hair later. The mixture is allowed to remain on the head for a period of time at ambient temperatures and is then removed by shampooing. The normal time of application is 20–30 minutes, but application times of from 10 minutes to one hour can be used.

The following Examples are given to further illustrate the present invention. It is to be understood, however, that this invention is not limited thereto.

The following terms appearing in the Examples or elsewhere in the specification have the definition ascribed to them also appearing below:

Miranol 2CM-SF: (Amphoteric 1); 1-hydroxyethyl-1-carboxymethyl-2-coco-imidazolinium betaine;

EDTA: Ethylenediamine tetraacetic acid;

Octoxynol-1: Polyoxyethylene(1)octylphenyl ether;

Nonoxynol-4: Polyoxyethylene(4)nonylphenyl ether; and

Nonoxynol-9: Polyoxyethylene(9)nonylphenyl ether. The fragrances may be eliminated from any of the formulas given in the table below and replaced with an equal quantity of water. All percentages are precent by weight unless otherwise specified.

The compositions of Examples 1 through 6 in Table II below are representative of the bases of the present invention. Example 2a is given for purposes of comparison. These bases can be prepared by mixing the ingredients listed in the aqueous carrier.

TABLE II

| | Base Formulations | | | | | | |
|---|---|---|---|---|---|---|---|
| Material | Ex. 1 | Ex. 2 | Ex. 3 | Ex. 4 | Ex. 5 | Ex. 6 | Ex. 2a |
| Linoleic diethanolamide | 5 | 5 | 5 | 30 | — | 10 | 5 |
| Miranol 2CM-SF | — | — | — | — | 15 | — | — |
| Ammonium hydroxide (28% NH$_3$) | — | — | — | 2 | — | — | — |
| Ethanolamine | 15 | 15 | 4 | — | — | 10 | 15 |
| Aminomethylpropanol | — | — | — | — | 2 | — | — |
| Hydrochloric acid (36%) | 7 | 7 | 2 | — | — | — | 7 |
| Carbitol | 5 | 5 | 8 | 3 | — | 3 | 5 |
| Propylene glycol | 3 | 3 | — | — | 3 | 2 | 3 |
| Hexylene glycol | — | — | 3 | 1 | 4 | — | — |
| Octoxynol-1 | 9 | 9 | 11 | 10 | 8 | 10.5 | 9 |
| Nonoxynol-4 | 2 | 2 | — | 5 | 4 | 2 | 2 |
| Nonoxynol-9 | 16 | 16 | 14 | — | — | 16.5 | 16 |
| Ethanol | 13 | 13 | — | — | — | 16 | 13 |
| Isopropanol | — | — | 9 | 8 | 7 | — | — |
| Stearyl trimethyl ammonium chloride | — | — | 5 | 7 | — | 2 | — |
| Soya trimethyl ammoniun chloride | — | 3.3 | — | — | 1.5 | — | 3.3 |
| Dilauryl dimethyl ammonium chloride | — | — | 1 | — | 1 | — | — |
| Distearyl dimethyl ammonium chloride | 1.2 | 1.2 | — | 0.7 | — | 1 | — |
| EDTA | 0.1 | 0.1 | 0.1 | 0.1 | 0.1 | 0.1 | 0.1 |
| Sodium sulfite | 0.2 | 0.2 | 0.2 | 0.2 | 0.2 | 0.2 | 0.2 |
| p-Phenylenediamine | 1.0 | 1.0 | — | 0.3 | 0.1 | 0.4 | 1.0 |
| Resorcinol | 0.8 | 0.8 | — | 0.4 | 0.1 | 0.4 | 0.8 |
| 2,4-diaminoanisole | 0.1 | 0.1 | — | — | 0.05 | 0.05 | 0.1 |
| Nitro-p-phenylenediamine | — | — | — | 0.2 | 0.05 | 0.05 | — |
| Fragrance | 0.2 | 0.2 | 0.2 | 0.2 | 0.2 | 0.2 | 0.2 |
| Water | 21.1 | 14.8 | 37.5 | 31.8 | 42.2 | 25.6 | 16.3 |

To prepare the composite compositions for use on hair, one part by volume of each of the base formulations of Examples 1 through 6 and 2a were mixed with one part by volume of a 6% aqueous solution of hydrogen peroxide immediately before use. Each composite composition so formed was shampooed into grey hair and left in contact therewith for 20–30 minutes at ambient temperatures and then washed out of the hair. The composite compositions formed from: (1) base formulation Examples 1 and 2 gave medium brown shades; (2) base formulation Example 3 a lightening of the hair was obtained; (3) base formulation Example 4 gave a light brown shade; (4) base formulation Example 5 gave a light ash brown dyeing; and (5) base formulation Example 6 gave a light brown dyeing. The composite composition from base formulation Example 2a gave dyeing similar to that obtained from base formulation Examples 1 and 2 i.e. medium brown.

It has been found that both the so-called mono-long chain alkyl and di-long chain alkyl quaternary amine compounds (e.g. [(Stearyl)N(CH$_3$)$_3$]Cl and [(Stearyl$_2$)N(CH$_3$)$_2$]Cl) respectively when incorporated in a hair treating composition containing an oxidizing agent, each show an improvement in the combability of hair treated with these compositions as compared with similar compositions that omit the quaternary amine compounds. However, quite unexpectedly it has been found that the di-long chain alkyl quaternary amine compounds are far superior to the mono-long chain alkyl quaternary amine compounds in this regard. It has further been found unexpectedly that a combination of the di-long chain alkyl quaternary amines and mono-long chain alkyl quaternary amines is superior to both the mono-long chain alkyl or di-alkyl long chain quaternary amines when used separately. This has been shown to be the case both by subjective evaluation of combability and feel of hair on live heads as well as by instrumental measuring of combing forces on hair swatches in the laboratory.

These findings have been demonstrated, for example, in the laboratory with respect to composite formulations formed from base formulations of Examples 1 and 2, on the one hand, and Example 2a on the other hand of Table II. Base formulation Example 1 contains as the di-long chain alkyl quaternary amine, distearyl dimethyl ammonium chloride. Base formulation Example 2 contains the di-long chain alkyl quaternary amine of Example 1 plus the long chain monoalkyl quaternary amine soya trimethyl ammonium chloride. Example 2a contains only a mono-long chain alkyl quaternary amine i.e. soya trimethyl ammonium chloride.

A volume of each of the aforesaid base formulations was thoroughly mixed with an equal volume of 6% aqueous hydrogen peroxide. Each composite composition so formed was applied to hair swatches for a period of from about 20-30 minutes at ambient temperatures. The hair swatches were then rinsed to remove the treating solution.

The combing force needed to pass a comb through each hair swatch was measured before treatment, after treatment when the hair was still wet and after treatment when the hair was dry. This was measured using an Instron Apparatus on which a comb was mounted.

The results obtained are given in Table III below. These are given as the average percent change in combability; the average being ascertained from about ten trials made with each composition. The percent change in combability is calculated using the following formula:

% change in combability = 100 × $\frac{\text{Combing force after treatment} - \text{Initial combing force}}{\text{Initial combing force}}$

TABLE III

| Treatment with Composite Composition containing | % Change in Combability | |
|---|---|---|
| | Wet | Dry |
| Formulation 1 | +32 | +11 |
| Formulation 2 | +2 | +16 |
| Formulation 2a | +75 | +65 |
| Commercial Oxidation Base Formula | +1300 | +63 |

As can be seen from Table III in going from a composition containing an oxidizing agent and a dialkyl long chain quaternary amine (Example 1) to a corresponding composition containing as the only quaternary amine a mono-alkyl long chain quaternary amine (Example 2a), the force necessary to comb hair after treatment for wet hair increased by about 43%. Similarly, in going from a composition containing an oxidizing agent in combination with a di-alkyl long chain quaternary amine and a mono-alkyl long chain quaternary amine (Example 2) to a corresponding composition containing as the only quaternary, a mono-alkyl long chain quaternary amine (Example 2a), the force necessary to comb hair after treatment increased about 73%.

Aside from the above quantitatively demonstrative improvement that follows from the use of compositions of the present invention i.e. compositions containing the di- long chain alkyl compounds, there are also improvements in actual use tests that are not so readily quantified. Thus, it has been found that under actual operating condition on live human heads, the improvement in combability can be perceived by the beauty operator when the composition of the present invention is compared with other similar compositions. This is particularly so when a composite composition containing Example 2 base of this invention is compared with similar composite compositions containing the Example 2a base.

Although the invention has been described with reference to specific forms thereof, it will be understood that many changes and modifications may be made without departing from the spirit of this invention.

What is claimed is:

1. A composition suitable for coloring hair comprising an aqueous vehicle containing an effective amount of an oxidizing agent, from about 0.05 to 5% by weight of a quaternary amine compound of the formula:

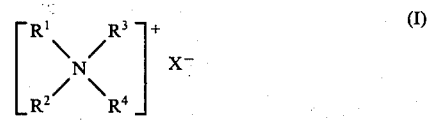

in which:
R¹ and R² are long chain aliphatic hydrocarbon radicals having about 10 to 26 carbons;
R³ and R⁴ are lower alkyl radicals having about 1 to 5 carbons;
X is an anion; and
an effective amount of an oxidation dye intermediate which develops a color under oxidative conditions; said composition containing sufficient alkalizing agent to give said composition a pH in the range of from 8 to 11.

2. A composition according to claim 1 wherein said oxidizing agent is present in the range of from about 0.5 to 20% by weight based on the weight of the composition.

3. A composition according to claim 1 wherein R¹ and R² are long chain alkyl groups.

4. A composition according to claim 1 also including up to 30% by weight of a neutral surfactant.

5. A composition according to claim 1 wherein the alkalizing agent is ethanolamine.

6. A composition according to claim 1 wherein the alkalizing agent is ammonium hydroxide.

7. A composition according to claim 1 wherein the quaternary amine compound is dilauryl dimethyl ammonium chloride.

8. A composition according to claim 1 wherein the quaternary amine is distearyl dimethyl ammonium chloride.

9. A composition according to claim 1 wherein the quaternary amine compound is dicoco dimethyl ammonium chloride.

10. A composition according to claim 1 wherein the quaternary amine compound is di-hydrogenated beef-tallow dimethyl ammonium chloride.

11. A composition according to claim 1 also including a second quaternary amine of formula:

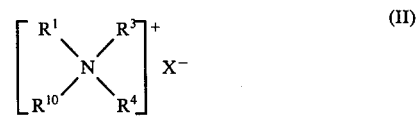

wherein:
R¹ is a long chain aliphatic hydrocarbon radical having about 10 to 26 carbons;
R³, R⁴ and R¹⁰ are lower alkyl radicals having 1 to 5 carbons; and
X is an anion.

12. A composition according to claim 11 wherein said second quaternary amine is soya trimethyl ammonium chloride.

13. A composition according to claim 1 in which the oxidizing agent is aqueous hydrogen peroxide.

14. A composition according to claim 1 in which said oxidation dye intermediate comprises an effective amount of a para component which is a compound selected from the group consisting of N-ethyl-N-hydroxyethyl-p-phenylenediamine and its hydrochloride; N,N-bis(β-hydroxyethyl)-p-phenylenediamine and its hydrochloride or sulfate; N,N-bis(β-hydroxyethyl)-3-methyl-p-phenylenediamine and its hydrochloride or sulfate; N,3-dimethyl-p-phenylenediamine and its hydrochloride; N-hydroxyethyl-2-methyl-p-phenylenediamine and its hydrochloride; N,2-dimethyl-p-phenylenediamine; N¹-methyl-3-methoxy-p-phenylenediamine; N¹-methyl-2-methoxy-p-phenylenediamine; 3-chloro-N¹-methyl-p-phenylenediamine; N,N-bis(2,3-dihydroxypropyl)-p-phenylenediamine; p-toluenediamine; p-aminophenol; p-aminodiphenylamine; 4-4'-diaminodiphenylamine; p-phenylenediamine; 2,6-dimethyl-p-phenylenediamine; 2,5-diaminopyridine and mixtures thereof.

15. A composition according to claim 14 wherein said compound is N,N-bis(β-hydroxyethyl)-p-phenylenediamine, its hydrochloride or its sulfate.

16. A composition according to claim 14 wherein said compound is p-phenylenediamine.

17. A composition according to claim 14 wherein said compound is p-aminophenol.

18. A composition according to claim 14 in which said oxidation dye intermediate further comprises as coupling component an effective amount of a phenol which reacts with said para component in the presence of oxidizing agents to produce indophenols.

19. A composition according to claim 18 wherein said phenol is resorcinol.

20. A composition according to claim 18 wherein said phenol is alpha-naphthol.

21. A composition according to claim 18 wherein said phenol is pyrocatechol.

22. A composition according to claim 18 wherein said phenol is pyrogallol.

23. A composition according to claim 14 in which said oxidation dye intermediate further comprises an effective amount of a m-phenylenediamine coupling component selected from the group consisting of m-phenylenediamine and 2,4-diaminoanisole.

24. A composition according to claim 14 in which said oxidation dye intermediate further comprises an effective amount of a coupling component selected from the group consisting of 2,4-diaminophenol, m-aminophenol, aminoresorcinol, 1,5-aminohydroxynaphthalene and 1,8-aminohydroxynaphthalene.

25. A composition according to claim 24 in which said coupling component is m-aminophenol.

26. A composition according to claim 14 in which said oxidation dye intermediate further comprises an effective amount of a coupling containing an active methylene group and selected from the group consisting of 3-methylpyrazolone-(5), 1-phenyl-3-methylpyrazolone-(5), 1,3-dimethylpyrazolone-(5), acetoacetic acid anilide, benzoylacetotoluide and nicotinoylacetanilide.

27. A composition according to claim 14 in which said oxidation dye intermediate further comprises an effective amount of a coupler selected from the group consisting of hydroquinone, catechol, 1,5-naphthalenediol, and o-aminophenol.

* * * * *

UNITED STATES PATENT AND TRADEMARK OFFICE
CERTIFICATE OF CORRECTION

PATENT NO. : 4,119,399
DATED : October 10, 1978
INVENTOR(S) : RAYMOND FEINLAND ET AL It is certified that error appears in the above—identified patent and that said Letters Patent are hereby corrected as shown below:

Column 2, line 27, after "carrier" delete the comma (,);

same line, change "therefore" to read

-- therefor -- .

Column 7, line 67, change "precent" to read

-- percent --.

Signed and Sealed this

Sixteenth Day of January 1979

[SEAL]

Attest:

RUTH C. MASON
Attesting Officer

DONALD W. BANNER
Commissioner of Patents and Trademarks